(12) United States Patent
Van Kruchten

(10) Patent No.: US 7,435,858 B2
(45) Date of Patent: Oct. 14, 2008

(54) PROCESS FOR THE PREPARATION OF ALKYLENE GLYCOLS

(75) Inventor: Eugene Marie Godfried Andre Van Kruchten, Amsterdam (NL)

(73) Assignee: Shell Oil Company, Houston, TX (US)

( * ) Notice: Subject to any disclaimer, the term of this patent is extended or adjusted under 35 U.S.C. 154(b) by 326 days.

(21) Appl. No.: 11/316,112

(22) Filed: Dec. 22, 2005

(65) Prior Publication Data

US 2006/0161026 A1  Jul. 20, 2006

(30) Foreign Application Priority Data

Dec. 23, 2004 (EP) .................................. 04258094

(51) Int. Cl.
*C07C 29/10* (2006.01)
*C07C 27/00* (2006.01)
*C07C 27/26* (2006.01)
*C07C 29/74* (2006.01)

(52) U.S. Cl. ....................... 568/867; 568/872

(58) Field of Classification Search ................. 568/867, 568/872
See application file for complete search history.

(56) References Cited

U.S. PATENT DOCUMENTS

| 4,982,021 A | 1/1991 | Best et al. ................. 568/867 |
| 5,488,184 A | 1/1996 | Reman et al. ............. 568/867 |
| 6,124,508 A | 9/2000 | Van Kruchten ........... 568/867 |
| 6,137,014 A | 10/2000 | Godfried Andere Van Kruchten ........... 568/867 |
| 6,137,015 A | 10/2000 | Strickler et al. ............ 568/867 |
| 6,153,801 A | 11/2000 | Van Kruchten ........... 568/867 |
| 6,156,942 A | 12/2000 | Lemanski et al. .......... 568/867 |
| 6,160,187 A | 12/2000 | Strickler et al. ............ 568/867 |
| 6,580,008 B2 | 6/2003 | Van Kruchten et al. .... 568/867 |
| 2002/0082458 A1 | 6/2002 | Peters et al. ................ 585/242 |
| 2005/0014980 A1 | 1/2005 | Van Hal et al. ............ 568/867 |
| 2005/0119510 A1 | 6/2005 | Boons et al. ............... 568/860 |

FOREIGN PATENT DOCUMENTS

| EP | 156449 | 10/1985 |
| EP | 0680943 | 11/1995 |
| EP | 1140749 | 10/2001 |
| EP | 1034158 | 8/2003 |
| JP | 56092228 | 7/1981 |
| WO | 95/20559 | 8/1995 |
| WO | 99/23053 | 5/1999 |
| WO | 99/31034 | 6/1999 |
| WO | 00/35840 | 6/2000 |
| WO | 00/35841 | 6/2000 |
| WO | 00/35842 | 6/2000 |
| WO | 02/098828 | 12/2002 |

OTHER PUBLICATIONS

European Patent Office Search Report dated Nov. 3, 2005 for application 04258094.4.
Shvets, V.F. et al, "The Cause and Quantitative Description of Catalyst Deactivation in the Ethylene Oxide Hydration Process", Chemical Engineering Journal, vol. 107, (2005), pp. 199-204; XP004816728 ISSN: 1385-8947.

*Primary Examiner*—Elvis O. Price

(57) ABSTRACT

A process for the production of alkylene glycol by hydrolysis of alkylene oxide with water is described wherein at least one reaction feed is first passed through a guard bed before entering a catalyst bed comprising hydrolysis catalyst.

35 Claims, 1 Drawing Sheet

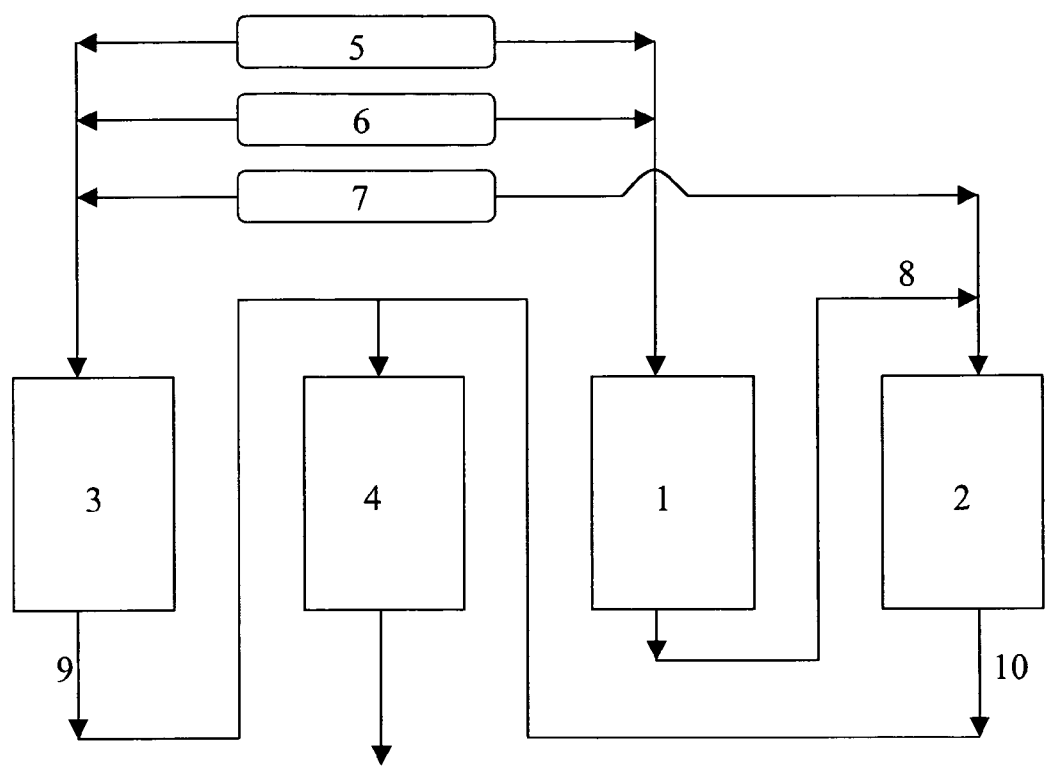

PROCESS FOR THE PREPARATION OF ALKYLENE GLYCOLS

CLAIM TO PRIORITY

This application claims the benefit of the filing date of EP 04258094.4 filed on Dec. 23, 2004.

FIELD OF THE INVENTION

The invention relates to a process for the preparation of alkylene glycols by catalytic hydrolysis.

BACKGROUND OF THE INVENTION

Alkylene glycols, in particular monoalkylene glycols, are of established commercial interest. For example, monoalkylene glycols are used in anti-freeze compositions, as solvents and as base materials in the production of polyalkylene terephthalates e.g. for fibers or bottles.

The production of alkylene glycols by liquid phase hydrolysis of alkylene oxide is known. The hydrolysis is generally performed by adding a large excess of water, e.g. 20 to 25 moles of water per mole of alkylene oxide. The reaction is considered to be a nucleophilic substitution reaction, whereby opening of the alkylene oxide ring occurs, water acting as the nucleophile. Because the primarily formed monoalkylene glycol also acts as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Considerable efforts have been made to find an alternative means for increasing the reaction selectivity without having to use a large excess of water. The hydrolysis of alkylene oxides to alkylene glycols can be performed with a smaller excess of water in a catalytic system. Therefore, these efforts have usually focused on the selection of more active hydrolysis catalysts and various catalysts have been disclosed in the literature.

Both acid and alkaline hydrolysis catalysts have been investigated, whereby it would appear that the use of acid catalysts enhances the reaction rate without significantly affecting the selectivity, whereas by using alkaline catalysts generally lower selectivities with respect to the monoalkylene glycol are obtained.

Catalytic processes, promoting a higher selectivity to monoalkylene glycol product at reduced water levels are known (e.g. EP-A-0,156,449, U.S. Pat. No. 4,982,021, U.S. Pat. No. 5,488,184, U.S. Pat. No. 6,153,801 and U.S. Pat. No. 6,124,508). Such catalysts generally comprise a strongly basic (anionic) exchange resin, often with quaternary ammonium or quaternary phosphonium electropositive complexing sites, coordinated with one or more anions (e.g. metalate, halogen, bicarbonate, bisulfite or carboxylate), and are generally most effective when used at elevated temperature.

A drawback shared by anionic exchange resins is, however, their limited tolerance to heat and their susceptibility to swelling. In International Patent Specification No. WO 02/098828 this swelling is attributed to thermal degradation of the catalyst resin and reaction of the resin with EO.

Catalyst swelling is problematic as it can result in the flow of reactants through the reactor being slowed or blocked. Therefore, efforts have been made to develop methods for reducing thermal swelling.

In the prior art, there are disclosed methods for reducing thermal swelling of hydrolysis catalysts.

In U.S. Pat. No. 6,137,015 it is described how processes comprising anion exchange resins, e.g. as described in U.S. Pat. No. 5,488,184, suffer from undesirable swelling, particularly at temperatures greater than 95° C. This document further describes a method of minimizing such swelling comprising adding to the reaction mixture a combination of additives comprising carbon dioxide and a base in an amount sufficient to maintain a pH between 5.0 and 9.0.

In EP-A-1,140,749, it is disclosed that enhancing the stability of basic ion exchange resins by adding a relatively small amount of an acidic ion exchange resin reduces catalyst swelling.

U.S. Pat. No. 6,160,187 proposes a method of minimizing the swelling of an anion exchange resin by using an adiabatic reactor.

US-A-2002/082456, describes a process for reducing the rate of swelling of an anion exchange resin-based catalyst by recycling reactor output from a reactor containing a catalyst based on an anion exchange resin back through the same reactor.

The efforts in the literature have thus concentrated on means to reduce thermal swelling which has hitherto been taught to be the major cause of catalyst swelling. However, despite the above proposals, the problem of reduction of catalyst swelling has not been adequately solved, and catalyst swelling is still a significant hindrance to the provision of a successful commercial-scale catalytic hydrolysis process, utilizing ion exchange resin catalysts.

SUMMARY OF THE INVENTION

The present invention provides a process for the preparation of an alkylene glycol by catalytic hydrolysis of the corresponding alkylene oxide, which comprises:
  i. contacting at least one feed comprising a product from a thermal hydrolysis of alkylene oxide comprising unreacted alkylene oxide with a guard bed comprising a solid compound capable of trapping trace compounds that induce catalyst swelling, to produce a treated feed; and,
  ii. contacting the treated feed with a catalyst bed comprising ion exchange resin-based hydrolysis catalyst.

In some embodiments, one or more further reaction feeds may also be contacted with the catalyst bed.

Also provided by the present invention is a process for the preparation of an alkylene glycol by catalytic hydrolysis of the corresponding alkylene oxide, which comprises:
  i. contacting at least one feed comprising alkylene oxide with a guard bed comprising a solid compound capable of trapping trace compounds that induce catalyst swelling to produce a treated feed; and
  ii. contacting a feed comprising the treated feed and at least one further reaction feed, comprising water, with a catalyst bed comprising ion exchange resin-based hydrolysis catalyst.

The present invention further provides a process for the preparation of an alkylene glycol by catalytic hydrolysis of the corresponding alkylene oxide, which comprises:

i. contacting at least one reaction feed with one of two or more separate guard beds, comprising a solid compound capable of trapping trace compounds that induce catalyst swelling which guard beds are contained within two or more separate vessels arranged in parallel and wherein said vessels have an associated switch or switches, to produce a treated feed; and ii. contacting a feed comprising said treated feed with a catalyst bed comprising ion exchange resin-based hydrolysis catalyst;

wherein at least one of the reaction feeds comprises alkylene oxide, and which process in addition comprises switching the feed at a predetermined time so that the feed is contacted with another of the two or more separate guard beds.

The present invention additionally provides the use of an ion exchange resin, in a process for the hydrolysis of alkylene oxide to the corresponding alkylene glycol, as a guard bed material to trap trace compounds that induce catalyst swelling.

BRIEF DESCRIPTION OF THE DRAWINGS

The drawing shows a schematic representation of the reactor line-up used in the Examples.

DETAILED DESCRIPTION OF THE INVENTION

The invention provides a process of diminishing a further type of catalyst resin swelling in the hydrolysis of alkylene oxides to alkylene glycols. Not wishing to be bound by any particular theory, this catalyst resin swelling is believed to be caused by impurities in conventional, commercial reaction feeds. These trace compounds appear to cause extreme and exponential swelling and degradation of the catalyst material. It has not previously been recognized that the catalyst resin swelling could be caused by such impurities.

Therefore, in the present invention, a guard bed comprising a solid compound capable of trapping the undesired compounds may be used in series with a catalyst bed comprising hydrolysis catalyst and at least one reaction feed is contacted with the guard bed before contacting the catalyst bed comprising hydrolysis catalyst (hereinafter referred to as 'the catalyst bed'). The use of a guard bed in catalytic hydrolysis of alkylene oxides has been found to reduce swelling of the hydrolysis catalyst to a significant extent, especially with commercial feeds, and to reduce any process disturbances originating from this type of swelling.

As used herein a 'guard bed' means a reaction bed, in series with the catalyst bed and upstream of said catalyst bed, comprising a means capable of removing, from the catalytic hydrolysis reaction feed, compounds that are injurious to the stability or activity of the catalyst. In the present invention, the guard bed comprises a solid compound capable of trapping compounds that result in extreme and exponential swelling of the catalyst. The person skilled in the art is readily able to identify a suitable solid compound that will in use eliminate or reduce exponential swelling of an ion exchange resin hydrolysis catalyst.

By a 'separate guard bed', a bed of catalyst, which is separate from, and not integral with, the hydrolysis catalyst, is intended.

As used herein the term 'trapping trace compounds' means removing the compounds from the reaction feed by chemical or physical means including, but not limited to, reaction of the compounds and absorption of the compounds.

In one embodiment of the invention the guard bed comprises a separate, easily removable upper section of catalyst, or separate guard bed, above the hydrolysis catalyst bed within the catalytic hydrolysis reactor.

In a preferred embodiment of the invention the guard bed is contained within a separate reactor vessel in series with a reactor vessel containing the catalyst bed.

In another preferred embodiment of the invention the guard bed comprises two or more, for example four, separate vessels arranged in parallel, with one or more associated switch(es) or switching means to allow the process to be switched between the vessels, thus maintaining continuous operation of the process. This arrangement allows for exhaustion of the solid compound in the guard bed during operation. Suitable switches or switching means that may be used in this embodiment are known to the skilled person. The feed may be switched between the parallel guard bed vessels when the solid compound capable of trapping trace compounds that induce catalyst swelling is exhausted, or at another predetermined time. A predetermined time is any suitable time period that ensures a continuous process operation for as long as possible, and may of course vary with the conditions of the process, for example the nature and amount of the guard bed material, the process temperature, etc. As a maximum, the predetermined time is when the catalyst bed is exhausted; the predetermined time may also be a fraction of this time. Alternatively, the pre-determined time may be when the hydrolysis catalyst is exhausted and needs replacing.

In an embodiment of the invention, the solid compound is selected from acidic ionic exchange resins, basic ion exchange resins, active carbon, thiosulfate on a solid support, molecular sieves, zeolites, silica gel, and one or more metals on a solid support, for example Mn/Cu on a monolith carrier, solid iron promoted alumina carrier or K/Pt on carbon.

In one preferred embodiment of the invention the solid compound in the guard bed is selected from strongly basic ion exchange resins, which may include bicarbonate, chloride, hydroxide, sulfate and thiosulfate forms, for example those known by the trademarks LEWATIT M 500 WS, AMBERJET 4200, DOWEX MSA-1, MARATHON-A, MARATHON-MSA and Reillex HPQ; weakly basic ion exchange resins, for example those known by the trademarks DUOLITE A 368, AMBERLYST A-21, AMBERLITE IRS-67, AMBERLITE IRA-94, AMBERLITE IRA-96, DOWEX 66, DIAION WA10, DIAION WA20, DIAION WA21J, DIAION WA30, PUROLITE A 100, PUROLITE 103, LEWATIT S 100 MB and LEWATIT S 100 G1; weakly acidic ion exchange resins, for example those known by the trademarks AMBERLITE IRC-50, AMBERLITE GC-50, AMBERLITE IRP-64, AMBERLITE IRP-88, AMBERLITE IRC-86, AMBERLITE IRC-76, IMAC HP 336 and LEWATIT CNP 80; strongly acidic ion exchange resins, for example those known by the trademarks AMBERLYST 15, AMBERJET 1500H, AMBERJET 1200H, DOWEX MSC-1, DIANON SK1B, LEWATIT VP OC 1812, LEWATIT S 100 MB and LEWATIT S 100 G1.

Catalysts that may be employed in the catalyst bed of the present process are known in the art. Preferred catalysts are those comprising an ion exchange resin as a solid support. More preferably, the catalyst comprises a basic ion exchange resin as a solid support, in particular the strongly basic (anionic) ion exchange resins wherein the basic groups are quaternary ammonium or quaternary phosphonium.

In a further preferred embodiment of the invention, both the guard bed and the catalyst bed comprise a strongly basic ion exchange resin. A very suitable such resin is a quaternary ammonium ion exchange resin having a bicarbonate anion, an example of which is AMBERJET 4200.

The term, 'reaction feeds' or 'feed' is intended to encompass any compound or mixture of compounds contacted with the catalyst bed during the reaction. In the present invention, one or more reaction feeds from a commercial plant may be used directly without any treatment or purification.

The present invention may be used for the catalytic hydrolysis of an alkylene oxide where the reaction feeds comprise water and the alkylene oxide. It can also apply to a process where the reaction feeds comprise the alkylene glycols and water product from a thermal alkylene oxide hydrolysis reactor with additional corresponding alkylene oxide, as necessary, from a direct oxidation process.

An alkylene oxide feed of the present invention may comprise purified alkylene oxide. This alkylene oxide may also be mixed with other reagents (for example, water). Furthermore, an alkylene oxide feed of the present invention may comprise alkylene oxide from a commercial alkylene oxide plant, either without further purification or after it has undergone one or more purification treatments, for example by distillation.

In the present invention, one or more of the reaction feeds is contacted with the guard bed before entering the catalyst bed.

In one embodiment of the invention, the feed comprising alkylene oxide is contacted with the guard bed before entering the catalyst bed. At least one further feed, comprising water, is then also fed into the catalyst bed. In one embodiment of the invention, the at least one further feed may comprise an alkylene glycols and water product from the thermal hydrolysis of the corresponding alkylene oxide.

In another embodiment of the invention, a feed comprising an alkylene glycols and water product from the thermal hydrolysis of the corresponding alkylene oxide is contacted with the guard bed before entering the catalyst bed. Such a feed may still contain sufficient unreacted alkylene oxide for conversion to glycols. However, when supplementary oxide is needed, a further reaction feed comprising alkylene oxide may also be contacted with the same or a different guard bed, or may be contacted with the catalyst bed without first contacting a guard bed.

The alkylene oxides used as starting material in the process of the invention have their conventional definition, i.e. they are compounds having a vicinal oxide (epoxy) group in their molecules.

Particularly suitable are alkylene oxides of the general formula,

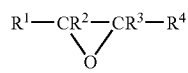

wherein $R^1$ to $R^4$ independently represent a hydrogen atom or an optionally substituted, alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$-$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane, 2,3-epoxybutane and glycidol. In the present invention the most preferred alkylene oxide is ethylene oxide.

The preparation of alkylene oxides is well known to the skilled person. In the case of ethylene oxide, it may be prepared by the well known direct oxidation of ethylene, i.e. by air or oxygen oxidation, utilizing silver-based catalysts and often also organic moderators, e.g. organic halides. However, any ethylene oxide feedstock from a commercial plant is suitable.

It is advantageous to perform the hydrolysis of the alkylene oxides without using excessive amounts of water. In the process according to the present invention, amounts of water, in the catalytic hydrolysis reactor, in the range of 1 to 15 moles per mole of alkylene oxide are quite suitable, amounts in the range of 1 to 6 on the same basis being preferred. In the process of the invention high selectivities with respect to the mono-alkylene glycol are often already achieved when only 4 or 5 moles of water per mole of alkylene oxide are supplied.

In certain embodiments of the present invention it may be beneficial to add carbon dioxide to the catalytic reactor. Such carbon dioxide may conveniently be added directly to the reactor or it may be added to one of the reaction feeds either before or after the guard bed. If carbon dioxide is to be added, the amount of carbon dioxide added may be varied to obtain optimum performance in relation to other reaction parameters, in particular the type of catalyst employed. However the amount added will preferably be less than 0.1% wt, more preferably less than 0.01% wt, based on a total amount of reactants in the catalytic reactor. In the reaction mixture, as determined by the content at the reactor outlet, the carbon dioxide content is suitably a maximum of 30 ppm, very suitably a maximum of 25ppm. The minimum amount present in the reaction mixture is conveniently in the order of 1-2 ppm of carbon dioxide.

The process of the invention may be carried out in batch operation. However, in particular for large-scale embodiments it is preferred to operate the process continuously.

Such continuous process may be carried out in fixed bed reactors, operated in up-flow or down-flow. Down-flow operation is preferred.

In a preferred embodiment, the present invention provides a continuous process for the preparation of an alkylene glycol by catalytic hydrolysis of the corresponding alkylene oxide, which comprises:

i) passing at least one feed comprising the product stream from the thermal hydrolysis of alkylene oxide through a separate guard bed comprising a solid compound capable of trapping trace compounds that induce catalyst swelling; and ii) passing the treated feed through a catalyst bed comprising ion-exchange resin-based hydrolysis catalyst.

In some embodiments, one or more further reaction feeds may also be contacted with the catalyst bed.

In another preferred embodiment, the present invention provides a continuous process for the preparation of an alkylene glycol by catalytic hydrolysis of the corresponding alkylene oxide, which comprises:

i) passing at least one feed comprising alkylene oxide through a separate guard bed comprising a solid compound capable of trapping trace compounds that induce catalyst swelling; and ii) passing the treated feed and at least one further reaction feed comprising water through a catalyst bed comprising ion exchange resin-based hydrolysis catalyst.

In an additional preferred embodiment, the present invention provides a continuous process for the preparation of an alkylene glycol by catalytic hydrolysis of the corresponding alkylene oxide, which comprises:

i) passing at least one reaction feed through one of two or more separate guard beds, comprising a solid compound capable of trapping trace compounds that induce catalyst swelling which guard beds are contained within two or more separate vessels arranged in parallel and wherein said vessels have associated switching means such that in operation the feed can be switched between the vessels; and ii) passing said treated feed and optionally at least one further reaction feed through a catalyst bed comprising ion exchange resin-based hydrolysis catalyst;

wherein at least one of the reaction feeds comprises alkylene oxide, and which process in addition comprises switching the feed at a predetermined time so that it passes through another of the two or more separate guard beds.

The reactors of the present invention may be maintained under isothermal, adiabatic or hybrid conditions. Isothermal reactors are generally shell- and tube reactors, mostly of the multi-tubular type, wherein the tubes contain the catalyst and a coolant passes outside the tubes. Adiabatic reactors are not cooled, and the product leaving them may be cooled in a separate heat exchanger.

In the process of the invention, the catalytic conversion of alkylene oxide may be incomplete, in which situation remaining alkylene oxide can be thermally hydrolyzed in the dead space of the reactor below the catalyst bed. Since this thermal hydrolysis is less specific towards alkylene glycol, minimizing the liquid hold-up in the reactor is preferred. This can be achieved by filling the reactor outlet part with internals or inert packing material to reduce its volume, and/or by adding an inert gas, such as nitrogen, to the reactor feed mixture and operating the reactor under so-called trickle flow conditions.

In order to obtain adequate time-yield values, it is recommended to perform the process under elevated temperature and pressure conditions.

Suitable reaction temperatures for the catalytic hydrolysis are generally in the range of from 70 to 200° C., whereby temperatures in the range of from 80 to 150° C. are preferred.

Depending on the solid compound capable of trapping trace compounds contained in the guard bed, and also the reaction feed to be treated, suitable reaction temperatures for the guard bed are in the range of from 0° C. to 200° C. The guard bed is suitably operated at a temperature at which the solid compound will not thermally decompose. Thus for an ion exchange resin catalyst, preferably the reaction temperature should not exceed 120° C.; for a zeolitic catalyst, the reaction temperature can exceed this. Where the reaction feed treated by the guard bed comprises alkylene oxide, a much lower temperature range is most useful.

In one preferred embodiment, a reaction feed comprising alkylene glycol and water product from the thermal hydrolysis of alkylene oxide is contacted with the guard bed comprising a strongly basic ion exchange resin before entering the catalyst bed, and the guard bed is operated at a temperature in the range of from 70 to 120° C.

In a further preferred embodiment, at least one reaction feed is contacted with a separate guard bed, comprising a solid compound capable of trapping trace compounds that induce catalyst swelling and then said treated feed and optionally at least one further reaction feed is contacted with a catalyst bed comprising ion exchange resin-based hydrolysis catalyst, wherein at least one of the reaction feeds comprises alkylene oxide and is contacted with a guard bed comprising a strongly basic ion exchange resin operated at a temperature in the range of from 0 to 60° C., preferably in the range of from 20 to 60° C., before entering the catalyst bed.

The reaction pressure in all of the reactors is usually selected in the range of from 200 to 3000 kPa, preferably in the range of from 200 to 2000 kPa. For batch operations of the process, the selected reaction pressure is advantageously obtained by pressurizing with an inert gas, such as nitrogen. If desired, mixtures of gases may be used, for example a mixture of carbon dioxide and nitrogen is in certain instances advantageous.

In a continuous process, the Liquid Hourly Space Velocity (LHSV) of the reaction is dependent on the catalyst and temperature of the reaction. The optimum LHSV for an individual reactor will also depend on the size of the reactor and the scale and capacity of a plant comprising said reactor. The LHSV of the reaction will preferably be in the range of from 0.5 to 20 l/l.h.

In order to accommodate any thermal swelling of the catalyst that may still occur during operation, the reactor volume can advantageously be greater than the volume occupied by of the catalyst therein, for example 10 to 70 vol % greater.

A problem which may occasionally arise in certain processes wherein ethylene oxide is being hydrolyzed is the presence of small amounts of amines and/or phosphines as impurities in the product. When a strongly basic anion exchange resin is used as the solid support for the catalytic anion, the basic groups thereof include quaternary ammonium or quaternary phosphonium groups. It has been found that during operation, small amounts of amines or phosphines tend to leach from the resin into the product. Amines in the product may also originate from corrosion inhibitors, which may be added to the water used in the process. Although the amounts of such amine or phosphine contaminants reaching the end-product are generally very small, they may affect the quality of the end-product such that it may be desirable to reduce the amounts to as low as possible so as not to affect the quality of the product. For example, trimethylamine (TMA) and/or dimethylamine (DMA) may reach the end product in an amount of up to 10 ppm while the fishy odor of TMA may be detected in an amount as low as 1 ppb.

An effective measure in removing amines and/or phosphines which may be present in the product of generally any process wherein ethylene oxide is being hydrolyzed, including the process of the present invention, has been found to be the use of a post-reactor bed, containing a strongly acidic ion exchange resin which effectively captures the amines or phosphines. Strongly acidic ion exchange resins may be of the sulfonic type. Commercially available examples are those known by the trademarks AMBERLYST 15, AMBERJET 1500H, AMBERJET 1200H, DOWEX MSC-1, DOWEX 50W, DIANON SK1B, LEWATIT VP OC 1812, LEWATIT S 100 MB and LEWATIT S 100 G1. Such strongly acidic ion exchange resins are available in $H^+$ form and in salt form, such as the $Na^+$ form. When only the $H^+$ form of the strongly acidic resin is used in the post-reactor guard bed, the product after contacting it may become acidic. Using a mixture of the strongly acidic ion exchange resin in its $H^+$ form and salt form has the advantage of the pH of the product remaining close to neutral.

An added advantage of the strongly acidic post-reactor bed is that any remaining alkylene oxide, which may be still present in the product, is hydrolyzed to alkylene glycol, albeit with a lesser selectivity towards the monoalkylene glycol.

In order to allow for exhaustion of the strongly acidic ion exchange resin during operation, it is advantageous to operate the post-reactor bed in two or more separate vessels, to allow the process to be switched between the two vessels, thus maintaining uninterrupted continuous operation.

Exhausted strongly acidic ion exchange resin can be regenerated by treatment with an acid, which is stronger than the sulfonic acid groups in the resin matrix, such as HCl and $H_2SO_4$. Hot sulfuric acid of 0.1 to 2 N has been proven to be effective.

The following Examples will illustrate the invention.

EXAMPLES

Four fixed bed reactors were used as follows:

Reactor 1 (separate guard bed) was filled with 30 mL of catalyst (AMBERJET 4200/bicarbonate—Rohm and Haas).

Reactor 2 (catalytic reactor—in series with separate guard bed Reactor 1) was filled with 30 mL of catalyst (AMBERJET 4200/bicarbonate—Rohm and Haas).

Reactor 3 (catalytic reactor—no separate guard bed) was filled with 30 mL of catalyst (AMBERJET 4200/bicarbonate—Rohm and Haas).

Reactor 4 (Post reactor) was filled with 30 mL of acidic resin (IRC-86—Rohm and Haas) to trap amines and convert the last trace of EO to EG. IRC-86 was replaced with AMBERLYST 15 (Rohm and Haas) after 2500 hours, as it showed poor activity in converting residual EO.

The reactors were connected as shown in the schematic reactor line-up of the drawing. In Example 1, ethylene glycol/water feed 5 and $CO_2$/water feed 6 were passed through the guard bed reactor 1 and the resultant reactor feed 8 was then added to catalytic reactor 2 along with ethylene oxide feed 7. In Example 2, reactor 3 received the ethylene glycol/water, $CO_2$/water and ethylene oxide feeds 5, 6 and 7 without the use of a separate guard bed. Reactor 4, utilized in both examples, contained a post-reactor bed to remove amines from the product streams 9 and 10 of catalytic reactors 2 and 3 and convert the final traces of EO.

Purified ethylene oxide (EO) feed 7 was used.

$CO_2$/water feed 6 was added to obtain 20 ppm $CO_2$ in the product streams 9 and 10 of the two EO-conversion reactors 2 and 3.

Ethylene glycol/water feed 5 from a large-scale thermal EO hydrolysis reactor was used, without purification, throughout the experiment, which was run with operating conditions as shown in Table 1. Until run hour 300, the flow rate of EO was 10 g/h; this was adjusted at run hour 300 to 7 g/h in order to expose the whole of the catalyst reactor beds in reactors 2 and 3 to EO.

TABLE 1

(Operating Conditions)

| | Reactor 1 (guard bed) | Reactor 2 (cat. reactor) | Reactor 3 (cat. reactor) | Reactor 4 (post-reactor) |
|---|---|---|---|---|
| Pressure (kPa) | 1100 | 1100 | 1100 | 1100 |
| Inlet temp (° C.) | 83.9 | 84.0 | 84.5 | 100-110 |
| Outlet temp (° C.) | 82.6 | 94.4 | 94.5 | 100-110 |
| $CO_2$(ppm in outlet) | 20.0 | 19.1 | 22.2 | 22.1 |
| LHSV (l/l · h) | 3.6 | 3.8 | 3.8 | 7.6 |
| $H_2O$/EO* (mol/mol) | — | 31 | 31 | >130 |
| Flow (g/h) | | | | |
| Water/glycol | 105-106 | — | 105-106 | — |
| Water/$CO_2$ | 4-5 | — | 4-5 | — |
| EO | — | 7 | 7 | — |
| Total | 110 | 117 | 117 | 234 |

*$H_2O$/EO ratio is calculated without the glycols in the feed

Once a week, samples were taken and swelling was measured.

Reactor 3 (no separate guard bed) blocked at run hours 1500 and 3000 at which points ~11-12% of the catalyst was removed and the reaction continued. Reactor 3 blocked again at run hour 5246 and the experiment was stopped.

Reactor 2 (with separate guard bed) blocked only at run hour 5314 and the experiment was stopped. At the end of the two experiments, the catalyst from both catalytic hydrolysis reactors 2 and 3 was removed and further analyzed.

Total swelling in reactor 3 (no separate guard bed) was 92.2% and total swelling for reactor 2 (with separate guard bed) was 74.8%. Even with ~11-12% of the catalyst removed at run hours 1500 and 3000 (which sample fractions did therefore not swell during the last part of the experiment), the total swelling of reactor 3 is higher than that of reactor 2.

A study has been made of the swelling of ion exchange resins and it has been found that swelling as a result of thermal degradation and subsequent incorporation of ethylene oxide occurs at a linear rate over time. The greatest swelling is found towards the bottom of the reactor. However, when exposed to commercial reaction feeds, surprisingly a second type of swelling can be differentiated by the character of the swelling and the characteristics of the swollen catalyst particles; it is believed that this swelling has occurred as a result of trace impurities in the feed.

The rate of swelling caused by trace impurities in the feed tends to have an exponential character over time. The greatest swelling generally occurs at the top of the reactor where the reaction feed first contacts the catalyst.

The catalyst in reactor 2 (with separate guard bed) experienced constant, linear swelling at 1.4%/100 h, indicative of swelling caused by thermal degradation of the catalyst. Further, analysis of the spent catalyst from reactor 2 (with separate guard bed) showed that the most-swollen fractions were fractions lower in the reactor, again indicative of thermal degradation of the catalyst.

The catalyst in reactor 3 (no separate guard bed) swelled at an increased rate, compared to reactor 2 (separate guard bed) and blocked up three times because of catalyst swelling before any blockage of reactor 2 had occurred. Analysis showed that the greatest swelling occurred at the top of the reactor, indicative of a large swelling contribution due to trace impurities in the feed.

Selectivity (corrected for glycols intake) remained high in both reactors throughout the experiment. Conversion levels also remained high, decreasing only towards the end of the experiment under extreme catalyst degradation conditions.

In conclusion, it was shown that the use of a separate guard bed greatly reduced the swelling attributed to trace impurities in the feed in a catalytic EO hydrolysis reactor.

In reactor 3, the removed small portion of the catalyst has acted as a guard bed, but frequent stoppage, opening of the catalyst bed, and then removal of the swollen upper part of a catalyst bed is impractical in a commercial scale operation, and the amount removed was, in any event, insufficient to prevent blockage again a short time later. Furthermore, by removing the swollen catalyst particles, a much-reduced amount of catalyst remains to perform the hydrolysis reaction, which is also highly undesirable in a commercial operation.

A separate, easily removable upper section of catalyst, or separate guard bed, above the hydrolysis catalyst bed within the catalytic hydrolysis reactor is, however, feasible and is contemplated within the scope of the present invention.

The most preferred system for a commercial scale system uses a separate guard bed system such as that used with

I claim:

1. A process for the preparation of an alkylene glycol by catalytic hydrolysis of the corresponding alkylene oxide, which comprises:
   i. contacting at least one feed comprising a product comprising alkylene oxide from a thermal hydrolysis of alkylene oxide with a guard bed comprising a solid compound capable of trapping trace compounds that induce catalyst swelling, to produce a treated feed; and,
   ii. contacting the treated feed with a catalyst bed comprising ion exchange resin-based hydrolysis catalyst.

2. The process of claim 1, further comprising contacting at least one further reaction feed with the catalyst bed.

3. The process of claim 2, wherein the at least one further reaction feed comprises alkylene oxide.

4. The process of claim 3, further comprising contacting the reaction feed comprising alkylene oxide with a guard bed comprising strongly basic ion exchange resin at a temperature in the range of from 0° C. to 60° C.

5. The process of claim 1, wherein the guard bed is contained within a first reactor vessel operated in series with a second reactor vessel containing said hydrolysis catalyst.

6. The process of claim 2, further comprising contacting the at least one further reaction feed with a guard bed comprising a solid compound capable of trapping trace compounds that induce catalyst swelling.

7. The process of claim 1, wherein the solid compound is selected from the group consisting of basic ion exchange resins, acidic ion exchange resins, active carbon, thiosulfate on a solid support, zeolites, silica gel and one or more metals on a solid support.

8. The process of claim 1, wherein the solid compound is selected from the group consisting of strongly basic ion exchange resins, weakly basic ion exchange resins, strongly acidic ion exchange resins and weakly acidic ion exchange resins.

9. The process of claim 1, further comprising contacting a reaction feed comprising a mixture of the corresponding alkylene glycol and water with a guard bed comprising strongly basic ion exchange resin at a temperature in the range of from 70° C. to 120° C.

10. The process of claim 1, wherein the alkylene oxide is of the general formula,

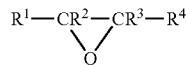

wherein R1 to R4 independently represent a hydrogen atom or an optionally substituted, alkyl group having from 1 to 6 carbon atoms.

11. The process of claim 9, wherein the alkylene oxide is ethylene oxide.

12. A process for the preparation of an alkylene glycol by catalytic hydrolysis of the corresponding alkylene oxide, which comprises:
   i. contacting at least one feed comprising alkylene oxide with a guard bed comprising a solid compound capable of trapping trace compounds that induce catalyst swelling to produce a treated feed; and
   ii. contacting a feed comprising the treated feed and at least one further reaction feed, comprising water, with a catalyst bed comprising ion exchange resin-based hydrolysis catalyst.

13. The process of claim 12, wherein the at least one further reaction feed comprises a product from a thermal hydrolysis of alkylene oxide.

14. The process of claim 13, wherein the guard bed is contained within a first reactor vessel operated in series with a second reactor vessel containing said hydrolysis catalyst.

15. The process of claim 12, wherein the guard bed is contained within a first reactor vessel operated in series with a second reactor vessel containing said hydrolysis catalyst.

16. The process of claim 12, further comprising contacting the reaction feed comprising alkylene oxide with a guard bed comprising strongly basic ion exchange resin at a temperature in the range of from 0° C. to 60° C.

17. The process of claim 12, further comprising contacting the at least one further reaction feed with a guard bed comprising a solid compound capable of trapping trace compounds that induce catalyst swelling.

18. The process of claim 12, wherein the solid compound is selected from the group consisting of basic ion exchange resins, acidic ion exchange resins, active carbon, thiosulfate on a solid support, zeolites, silica gel and one or more metals on a solid support.

19. The process of claim 12, wherein the solid compound is selected from the group consisting of strongly basic ion exchange resins, weakly basic ion exchange resins, strongly acidic ion exchange resins and weakly acidic ion exchange resins.

20. The process of claim 12, further comprising contacting the reaction feed comprising alkylene oxide with a guard bed comprising strongly basic ion exchange resin at a temperature in the range of from 0° C. to 60° C.

21. The process of claim 12, further comprising contacting a reaction feed comprising a mixture of the corresponding alkylene glycol and water with a guard bed comprising strongly basic ion exchange resin at a temperature in the range of from 70° C. to 120° C.

22. The process of claim 12, wherein the alkylene oxide is of the general formula,

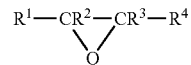

wherein $R^1$ to $R^4$ independently represent a hydrogen atom or an optionally substituted, alkyl group having from 1 to 6 carbon atoms.

23. The process of claim 22, wherein the alkylene oxide is ethylene oxide.

24. A process for the preparation of an alkylene glycol by catalytic hydrolysis of the corresponding alkylene oxide, which comprises:
   i. contacting at least one reaction feed with one of two or more separate guard beds, comprising a solid compound capable of trapping trace compounds that induce catalyst swelling which guard beds are contained within two or more separate vessels arranged in parallel and wherein said vessels have an associated switch or switches, to produce a treated feed; and
   ii. contacting the treated feed with a catalyst bed comprising ion exchange resin-based hydrolysis catalyst;

wherein at least one of the reaction feeds comprises alkylene oxide, and wherein at a predetermined time the feed is switched so that it passes through another of the two or more separate guard beds.

25. The process of claim 24, further comprising contacting at least one further reaction feed with the catalyst bed.

26. The process of claim 25, wherein the at least one reaction feed comprises alkylene oxide.

27. The process of claim 24, further comprising contacting the reaction feed comprising alkylene oxide with a guard bed comprising strongly basic ion exchange resin at a temperature in the range of from 0° C. to 60° C.

28. The process of claim 25, further comprising contacting the at least one further reaction feed with a guard bed comprising a solid compound capable of trapping trace compounds that induce catalyst swelling.

29. The process of claim 24, wherein the solid compound is selected from the group consisting of basic ion exchange resins, acidic ion exchange resins, active carbon, thiosulfate on a solid support, zeolites, silica gel and one or more metals on a solid support.

30. The process of claim 24, wherein the solid compound is selected from the group consisting of strongly basic ion exchange resins, weakly basic ion exchange resins, strongly acidic ion exchange resins and weakly acidic ion exchange resins.

31. The process of claim 30, wherein the solid support is a strongly basic ion exchange resin.

32. The process of claim 24, further comprising contacting a reaction feed comprising a mixture of the corresponding alkylene glycol and water with a guard bed comprising strongly basic ion exchange resin at a temperature in the range of from 70° C. to 120° C.

33. The process of claim 24, wherein the alkylene oxide is of the general formula,

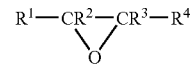

wherein $R^1$ to $R^4$ independently represent a hydrogen atom or an optionally substituted, alkyl group having from 1 to 6 carbon atoms.

34. The process of claim 33, wherein the alkylene oxide is ethylene oxide.

35. The process of claim 24, wherein the process is a continuous process.

* * * * *